United States Patent
Beech et al.

(10) Patent No.: US 10,363,316 B2
(45) Date of Patent: *Jul. 30, 2019

(54) PHARMACEUTICAL FORMULATION COMPRISING NSAID AND CYCLODEXTRIN

(71) Applicant: Reckitt Benckiser Healthcare International Limited, Berkshire (GB)

(72) Inventors: Edward Beech, Hull (GB); Alden Rodwell, Hull (GB); Mark Squires, Hull (GB)

(73) Assignee: RECKITT BENCKISER HEALTHCARE (UK) LIMITED, Slough Berkshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/859,619

(22) Filed: Sep. 21, 2015

(65) Prior Publication Data

US 2016/0008478 A1    Jan. 14, 2016

Related U.S. Application Data

(63) Continuation of application No. 13/993,320, filed as application No. PCT/GB2011/052457 on Dec. 12, 2011, now Pat. No. 9,138,482.

(30) Foreign Application Priority Data

Dec. 15, 2010  (GB) .................................. 1021267.8

(51) Int. Cl.
| | |
|---|---|
| A61K 47/40 | (2006.01) |
| A61K 31/192 | (2006.01) |
| A61K 31/196 | (2006.01) |
| A61K 47/02 | (2006.01) |
| A61K 9/00 | (2006.01) |
| A61K 9/08 | (2006.01) |
| A61K 9/12 | (2006.01) |
| B82Y 5/00 | (2011.01) |
| A61K 47/69 | (2017.01) |

(52) U.S. Cl.
CPC .............. *A61K 47/40* (2013.01); *A61K 9/006* (2013.01); *A61K 9/08* (2013.01); *A61K 9/12* (2013.01); *A61K 31/192* (2013.01); *A61K 31/196* (2013.01); *A61K 47/02* (2013.01); *A61K 47/6951* (2017.08); *B82Y 5/00* (2013.01)

(58) Field of Classification Search
CPC ...... A61K 47/40; A61K 31/192; A61K 9/006; A61K 9/08
See application file for complete search history.

(56) References Cited

U.S. PATENT DOCUMENTS

| | | | | |
|---|---|---|---|---|
| 5,024,997 | A | | 6/1991 | Motola et al. |
| 6,166,083 | A | * | 12/2000 | Barrett ................. A61K 9/0056 514/570 |
| 9,138,482 | B2 | * | 9/2015 | Beech .................. A61K 31/192 |
| 2006/0120967 | A1 | * | 6/2006 | Namburi .............. A61K 9/0043 424/45 |
| 2007/0232567 | A1 | | 10/2007 | Wright | |

FOREIGN PATENT DOCUMENTS

| | | |
|---|---|---|
| CN | 101559077 A | 10/2009 |
| EP | 0490193 A1 | 6/1992 |
| EP | 1574221 A1 | 9/2005 |
| EP | 1974751 A1 | 10/2008 |
| JP | 56034618 A | 8/1979 |
| WO | 9200725 A1 | 1/1992 |
| WO | 9504528 A2 | 2/1995 |
| WO | 9507104 A1 | 3/1995 |
| WO | 9718245 A1 | 5/1997 |
| WO | 9718802 A1 | 5/1997 |
| WO | 9852540 A1 | 11/1998 |
| WO | 2004050123 A2 | 6/2004 |
| WO | 2005079858 A1 | 9/2005 |
| WO | 2009089269 A1 | 7/2009 |

OTHER PUBLICATIONS

CSER issued Mar. 11, 2011 for priority GB application 1021267.8.
CSER issued Mar. 20, 2012 for priority GB application 1121476.4.
Guan, P. et al., WPIIThomson, vol. 2009, Nr: 73, Publication No. XP-002674166.
International Search Report and Written Opinion dated May 3, 2012 for priority application PCTIGB2011/052457.
Kiyoshi Masuda, "Protective Effects of Cyclodextrin for the Local Irritation Induced by Aqueous Preparations of Flurbiorofen," Yakugaku Zasshi, Feb. 1, 1984, pp. 1075-1082.
Moore, N., Dr. et al, "Tolerabiilty of Ibuprofen, Aspirin and Paracetamol for the Treatment of Cold and Flu Symptoms and Sore Throat Pain," IJCP, vol. 56, No. 10, Dec. 2002, pp. 732-734, Publication No. XP009031180.
Ozaki et al., "Transdermal ketoprofen mitigates the severity of postoperative sore throat," Canadian Journal of Anesthesia, vol. 48, No. 11, Dec. 1, 2001, pp. 1080-1083.

* cited by examiner

*Primary Examiner* — James D. Anderson
(74) *Attorney, Agent, or Firm* — Troutman Sanders LLP; Ryan Schneider; Chris Davis (57) ABSTRACT

A liquid throat spray composition for topical application to a sore throat including an aqueous solution of an NSAID and cyclodextrin.

28 Claims, 5 Drawing Sheets

PHARMACEUTICAL FORMULATION COMPRISING NSAID AND CYCLODEXTRIN

CROSS-REFERENCE TO RELATED APPLICATIONS

This application is a continuation of U.S. Ser. No. 13/993,320 filed 2 Jul. 2013, which application is a US National Stage of International Application No. PCT/GB2011/052457, filed 12 Dec. 2011, which application claims the benefit of GB 1021267.8, filed 15 Dec. 2010, all herein fully incorporated by reference.

BACKGROUND OF THE INVENTION

1. Field of Invention

The present invention is directed to a pharmaceutical composition in the form of a spray/aerosol which can be used to deliver unpalatable compounds, such as NSAIDs. In particular, the present invention is directed to a flurbiprofen-based spray.

2. Background and Related Art

Flurbiprofen is a member of the phenylalkanoic acid derivative family of non-steroidal anti-inflammatory drugs (NSAIDs) used to treat inflammation and pain. It is predominately used in the treatment of rheumatoid arthritis due to its anti-inflammatory effect.

Flurbiprofen is very insoluble in low pH aqueous solution, and its solubility increases slightly as the pH increases. Flurbiprofen has varying solubility in different organic solvents. Different formats and applications of flurbiprofen have been developed, such as flurbiprofen lozenges used in the treatment of sore throats. Mouthwashes containing flurbiprofen have also been developed; as well as mouth sprays that deliver a low (<0.5% w/v) level of the active Flurbiprofen is known for producing a burning sensation in the buccal cavity (the mouth). This flurbiprofen related burn is extremely unpleasant causing an irritating prickly sensation at the back of the throat as well as a cough, gag, tickle or irritation depending on its concentration. It is desirable to reduce this 'burn' in flurbiprofen-containing products, and there has been considerable effort in this area. For example, there has been much effort in developing flavors that mask the burn with various flavors. The absence of taste receptors at the back of the throat and the ineffectiveness of flavors to cover the burn appear to confirm that the issue to be addressed is the irritating effect of flurbiprofen on pain receptors at the back of the throat.

Cyclodextrins are a family of compounds which are saccharide polymers. These sugar derivatives are formed from differing numbers of sugars bound together to form a cyclic oligosaccharide. As can be seen below α-CD consists of 6 membered sugar ring while β-CD and γ-CD consist of a 7 and 8 membered sugar ring respectively. Cyclodextrins are produced from starch by means of enzymatic conversion. The cyclic structure provides the cyclodextrin molecule with a large surface area, and also allows other smaller molecules to enter it forming an inclusion complex; this provides endless potential uses for cyclodextrins.

The cyclodextrin's ability to form complexes by "encapsulating" other molecules has plenty of applications, such as in drug delivery systems.

Liquid compositions which comprise an NSAID and a cyclodextrin are known in the art. For example, WO 92/00725 discloses compositions which contain ketoprofen, a cyclodextrin and dimethyl isosorbide. The presence of the isosorbide provides the composition with anti-plaque properties and enhances the anti-inflammatory properties.

WO 95/04528 discloses powder compositions containing a complex of an NSAID and a cyclodextrin for re-formulation with water to form a drink. The composition requires the presence of an acid/base couple to ensure that the complex of NSAID and cyclodextrin dissolves. A similar composition is described in WO 95/07104.

U.S. Pat. No. 5,042,997 describes an ibuprofen-containing liquid. The compositions disclosed therein are not suitable for use in a spray format. A similar composition is described in WO 2005/079858.

EP 1 574 221 describes an injectable composition which comprises diclofenac. Similarly, WO 2009/089269 describes a method of treating pain in subjects with increased risk of significant blood loss. The compositions disclosed therein comprise diclofenac and a cyclodextrin, and are most suitable for injection.

EP 1 974 751 discloses a composition which comprise an NSAID, a cyclodextrin and an amine. The presence of the amine results in the formation of an amine salt which improves the solubility of the NSAID.

Yet, none of these prior art documents describes a composition which is suitable for use as a spray to treat sore throat.

Liquid compositions which comprise an NSAID and a cyclodextrin are known in the art. Typically, these compositions can be in the form of powders that require reconstitution to form a product in the form of a consumable drink or an injectable liquid. Prior art compositions can also include specific excipients which either enhance their anti-inflammatory effect or improve the solubility of the NSAID.

Yet, none of these prior art documents describes a composition which is suitable for use as a spray to treat sore throat.

BRIEF SUMMARY OF THE INVENTION

Briefly described, in a preferred form, the present invention provides a significantly higher concentration of NSAID per fluid volume than compositions that are currently available.

According to a first aspect of the present invention there is provided a liquid composition in comprising an aqueous solution of an NSAID and one or more cyclodextrins.

Typically the NSAID is selected from the group consisting of ibuprofen, ketoprofen, flurbiprofen, diclofenac, naproxen. Preferably the NSAID can be selected from ketoprofen or flurbiprofen. Most preferably the NSAID is flurbiprofen.

The cyclodextrin can be selected from α, β, γ cyclodextrin and derivatives thereof. Cyclodextrins for use in the present invention include the natural cyclodextrins and their derivatives, including the alkylated and hydroxyalkylated derivatives and the branched cyclodextrins. derivatives bearing sugar residues are of special interest. Especially useful herein are the hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α, β, γ,-cyclodextrin. Specific cyclodextrin derivatives for use herein include methyl α cyclodextrin, hydroxyethyl α cyclodextrin, hydroxypropyl α cyclodextrin, dihydroxypropyl α cyclodextrin, methyl β cyclodextrin, hydroxyethyl β cyclodextrin, hydroxypropyl β cyclodextrin, dihydroxypropyl β cyclodextrin, methyl γ cyclodextrin, hydroxyethyl γ cyclodextrin, hydroxypropyl γ cyclodextrin and dihydroxypropyl γ cyclodextrin.

The ratio of the NSAID to cyclodextrin is between 1:0.5 and 1:1.5. The ratio can be between 1:0.7 and 1:1. A preferred ratio is 1:0.87. For the avoidance of doubt, the ratios for NSAID and cyclodextrin are molar ratios.

The composition comprises the NSAID at a level of at least 1% w/v. The composition can contain 1-5% w/v. The composition preferably contains no more than 3.2% NSAID. The composition can contain a most preferred amount of NSAID is 1.6% w/v. In an alternative embodiment the preferred amount is 3.13% NSAID.

Typically the composition contains a buffer. The term "buffer" refers to a pharmaceutically acceptable excipient that helps to maintain the pH of the solution within a particular range specific to the buffering system. The buffer is present for example at a concentration in the range from about 0.03% to about 5.0% w/v, or about 0.1% to about 2.0% w/v. Non-limiting illustrative examples of pharmaceutically acceptable buffering agents include phosphates, ascorbates, acetates, citrates, tartrates, lactates, succinates, amino acids and maleates. Particularly preferred buffers are disodium hydrogen orthophosphate, citric acid or combinations thereof.

The pH of a composition in preferred embodiments is generally from about 6 to about 9. Typically, the pH of the liquid formulation is about 7.4. Alternatively, the pH of the liquid formulation may be selected from the following ranges: 6.5 to 8.5; 7.0 to 8.0; and 7.2 to 7.6.

The composition can further contain a thickening agent such as hydroxy ethyl cellulose, hydroxy propyl methyl cellulose, sodium carboxy methyl cellulose or hydroxy propyl cellulose.

Minor amounts of other ingredients such as pH adjusters (e.g., a base such as NaOH), emulsifiers or dispersing agents, preservatives, sweeteners, and flavorants may also be present.

A preferred composition according to the present invention comprises:
1-5% flurbiprofen;
5-10% one or more α, β, γ cyclodextrins and derivatives thereof;
up to 5% one or more aqueous buffers; and
80-90% water.

The composition may further comprise up to 1% one or more flavorants, up to 0.2% sweetener and up to 0.5% preservatives.

The composition may further comprise up to 0.5% thickening agent.

The composition can be used in a spray format, or as part of a gargle or mouthwash. A preferred format is as a sprayable liquid.

The composition can be provided as a unit dose of up to about 2 ml. The composition can be provided as a unit dose of up to about 1 ml. The composition can be provided as a unit dose of up to about 0.5 ml. The composition can be provided as a unit dose of up to about 0.4 ml. The composition can be provided as a unit dose of up to about 0.3 ml. The composition can be provided as a unit dose of up to about 0.2 ml. The composition can be provided as a unit dose of up to about 0.1 ml.

A dose can comprise one or more sub-doses. Typically, the dose can comprise 1-5 sub-doses. The dose can comprise two or three sub-doses. By way of example, if the dose is 0.6 ml, then it can comprise 6×0.1 ml sub-doses, 4×0.15 ml sub-doses, 3×0.2 ml sub-doses, 2×0.3 ml sub-doses, or 1×0.6 ml dose.

In an exemplary embodiment, a dose comprises three sub-doses, being three sprays of 0.18 ml, to give a total of 0.54 ml.

According to another aspect of the present invention there is provided the use of a pharmaceutical composition as described in the first aspect of the invention for the treatment of sore throat.

According to another aspect of the present invention there is provided a method of treating a sore throat using a formulation as described in the first aspect of the invention.

According to another aspect of the present invention there is provided a method of reducing the irritation or burn associated with flurbiprofen comprising administering to an individual a composition in accordance with the first aspect of the present invention.

According to another aspect of the present invention there is provided a method of improving the stability of flurbiprofen when in solution wherein the solution includes compounds bearing a hydroxyl group which do not act as a solvent and wherein the method includes the step of mixing the flurbiprofen with a cyclodextrin prior to addition of the compounds bearing a hydroxyl group.

Typically the solution containing the flurbiprofen is an aqueous solution.

Typically the method is used to form a composition in accordance with the first aspect of the present invention.

These and other objects, features and advantages of the present invention will become more apparent upon reading the following specification in conjunction with the accompanying drawing figures.

BRIEF DESCRIPTION OF THE DRAWINGS

Embodiments of the present invention will be now described by way of example only with reference to the accompanying drawings in which.

DETAILED DESCRIPTION OF THE PREFERRED EMBODIMENTS

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

As used herein, the term "consisting essentially of" means the composition contains the indicated components and may contain additional components provided that the additional components that are non-active and do not materially affect the composition's basic characteristics. As used herein, the term "consisting of" means the composition contains the only indicated components and excludes other components.

As used herein, the term "up to" means that the component is present in the composition to the level of the value given. For example, the term "up to 5%" would mean that a component is present at a level greater than 0% and less than or equal to about 5%.

EXAMPLE 1

1.683 g of flurbiprofen and 6.265 g of beta cyclodextrin (BCD) were weighed into a 100 ml volumetric flask. 50 ml of pH 7.4 buffer solution was added to the volumetric flask and shaken to suspend and wet the BCD and flurbiprofen. 1 M NaOH (aq) was added dropwise with vigorous stirring until the flurbiprofen and beta cyclodextrin dissolved fully. 6 ml of NaOH solution was required to dissolve the BCD and flurbiprofen. The solution was made up to 100 ml with purified water and mixed well. The solution was clear and colorless. The pH was measured and found to be pH 7.40 exactly.

Additional examples were prepared in a similar way. Details of these compositions are given below.

| Material Name | Example 2 (% w/w) | Example 3 (% w/w) | Example 4 (% w/w) | Example 5 (% w/w) |
| --- | --- | --- | --- | --- |
| Flurbiprofen | 1.62 | 1.62 | 1.62 | 1.62 |
| Beta Cyclodextrin | 6.04 | 6.04 | 4.228 | 4.228 |
| Disodium Hydrogen Orthophosphate | 3.1825 | 3.1825 | 3.1825 | 3.1825 |
| Citric Acid Monohydrate | 0.11655 | 0.11655 | 0.11655 | 0.11655 |
| Methyl p-hydroxybenzoate | 0.2187 | 0.2187 | 0.2187 | 0.2187 |
| Propyl p-hydroxybenzoate | 0.04374 | 0.04374 | 0.04374 | 0.04374 |
| Sodium Hydroxide | 0.24 | 0.24 | 0.24 | 0.24 |
| Mint Flavor | 0.20 | 0.20 | 0.20 | 0.20 |
| Cherry Flavor | 0.25 | 0.25 | 0.25 | 0.25 |
| Hydroxyethyl Cellulose | — | 0.20 | — | — |
| WS-23 | — | — | 0.10 | 0.10 |
| Sodium Saccharin | 0.05 | 0.05 | 0.05 | 0.05 |
| Hydroxypropyl Beta Cyclodextrin | — | — | 2.238 | — |
| Methyl Beta Cyclodextrin | — | — | — | 2.24 |
| Purified Water | 88.03851 | 87.83851 | 87.5125 | 87.51051 |
| TOTAL | 100.00 | 100.00 | 100.00 | 100.00 |

Figure 1:
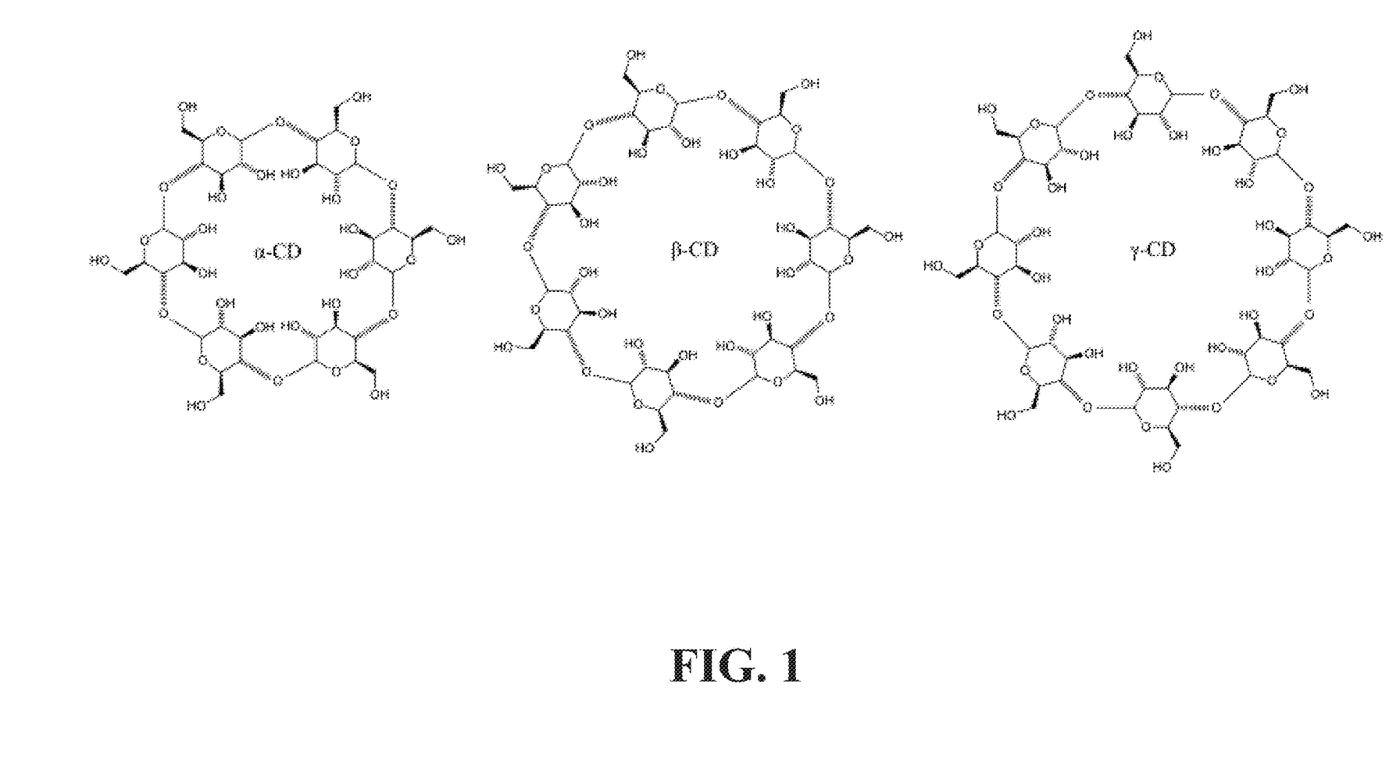
FIG. 1 illustrates α, β, γ cyclodextrin.
Figure 2:
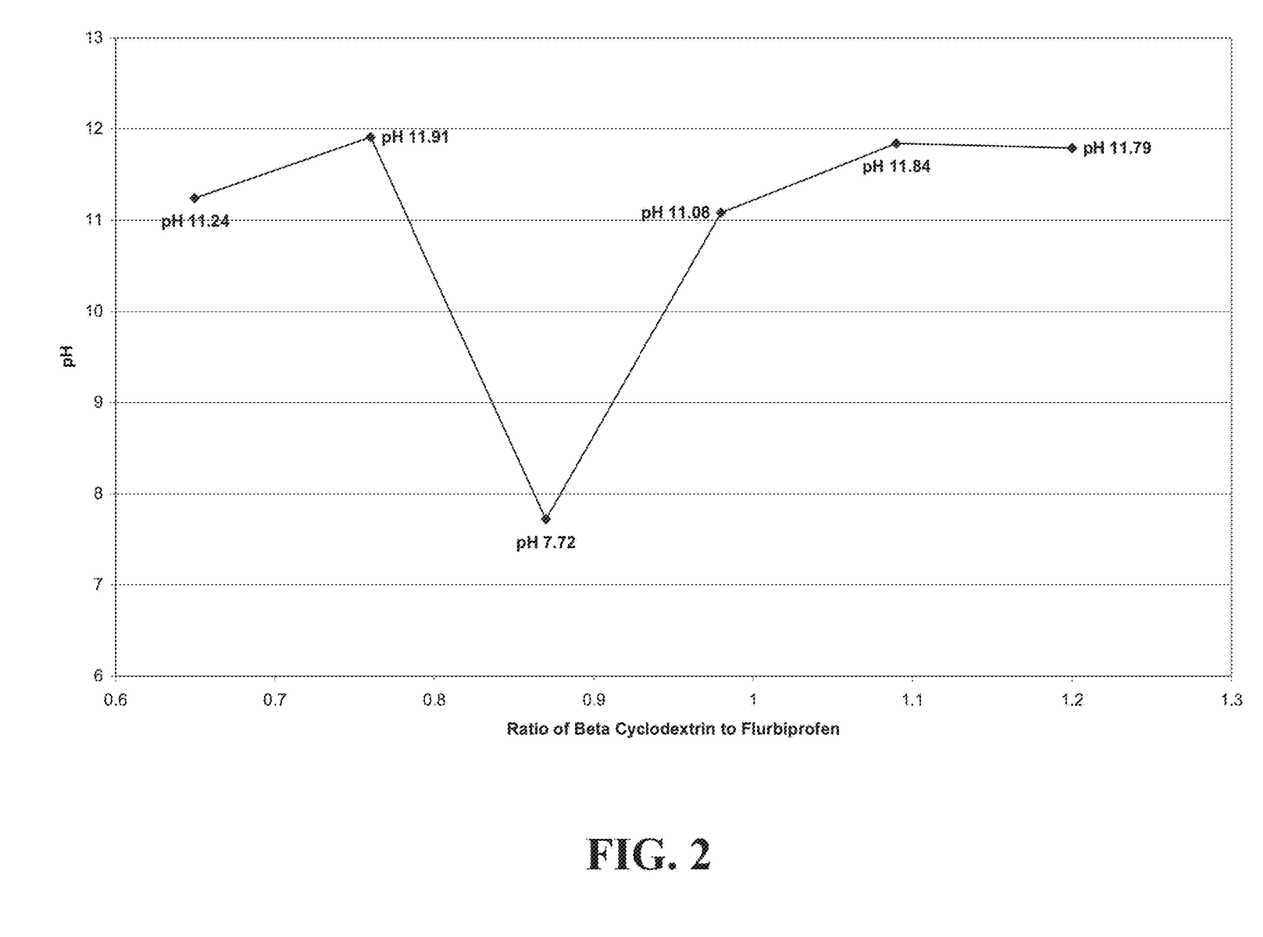
FIG. 2 illustrates the minimum pH required to achieve solution clarity for different beta cyclodextrin:flurbiprofen ratios at a flurbiprofen concentration of 14.58 mg/ml.

FIG. 2 illustrates the minimum pH required to achieve solution clarity for different beta cyclodextrin:flurbiprofen ratios and the effect of variation of the ratio of BCD to flurbiprofen on the minimum pH required as a result of gradual addition of 1M NaOH to obtain clarity. The required pH remains high until a ratio of about 0.75:1, at which point there is a dip in the threshold pH until the ratio is 1:1. The dip centers at a ratio of 0.87:1 BCD:Flurbiprofen. The flurbiprofen concentration is fixed at 8.75 mg per 600 µl.

Figure 3:
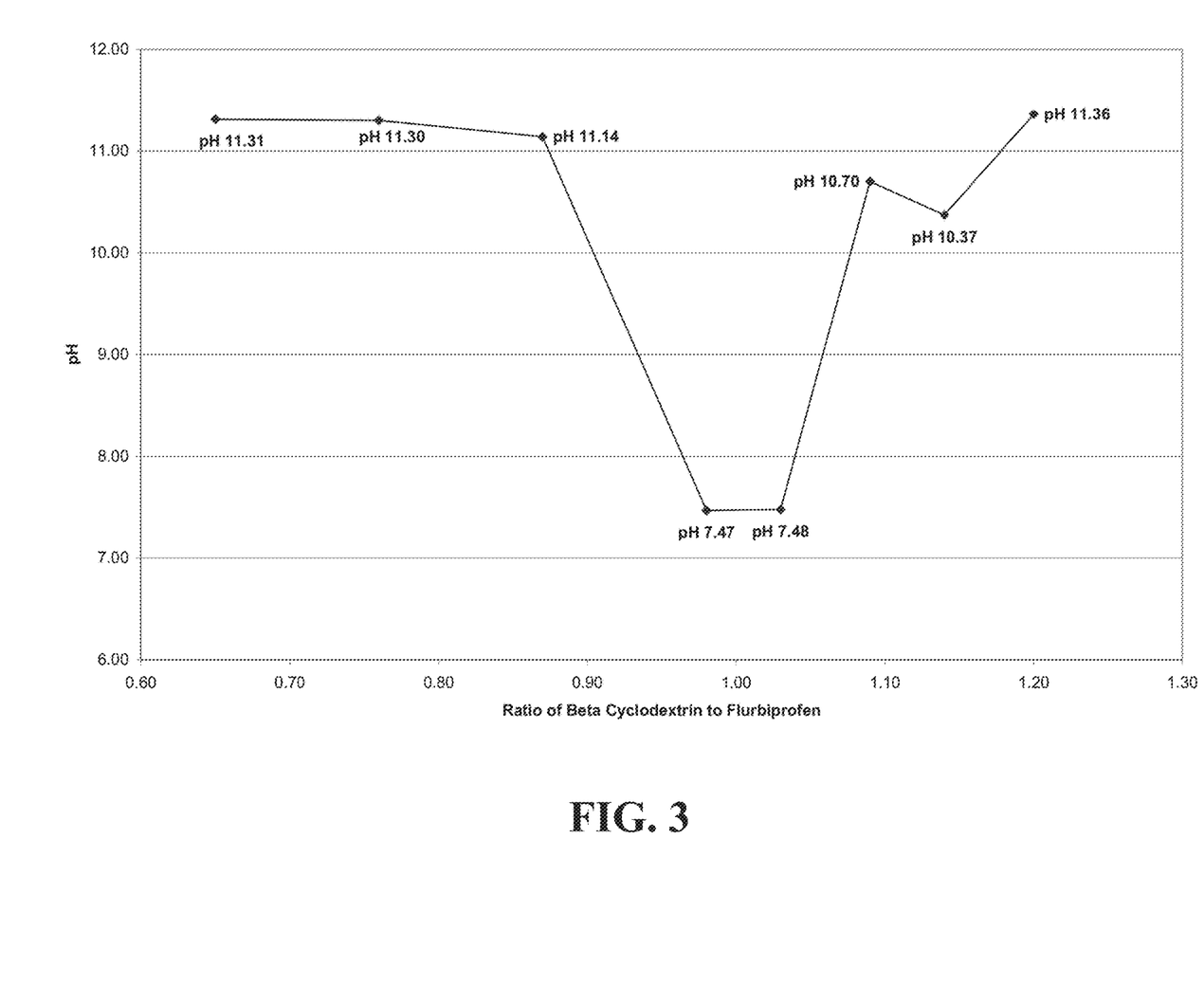
FIG. 3 illustrates the minimum pH required to achieve solution clarity for different beta cyclodextrin:flurbiprofen ratios at a flurbiprofen concentration of 31.25 mg/ml.

FIG. 3 illustrates the change in minimum required pH observed at a higher concentration of flurbiprofen. The dip in threshold pH centers at BCD:Flurbiprofen ratios of 0.95:1 to 1.05:1.

Figure 4:
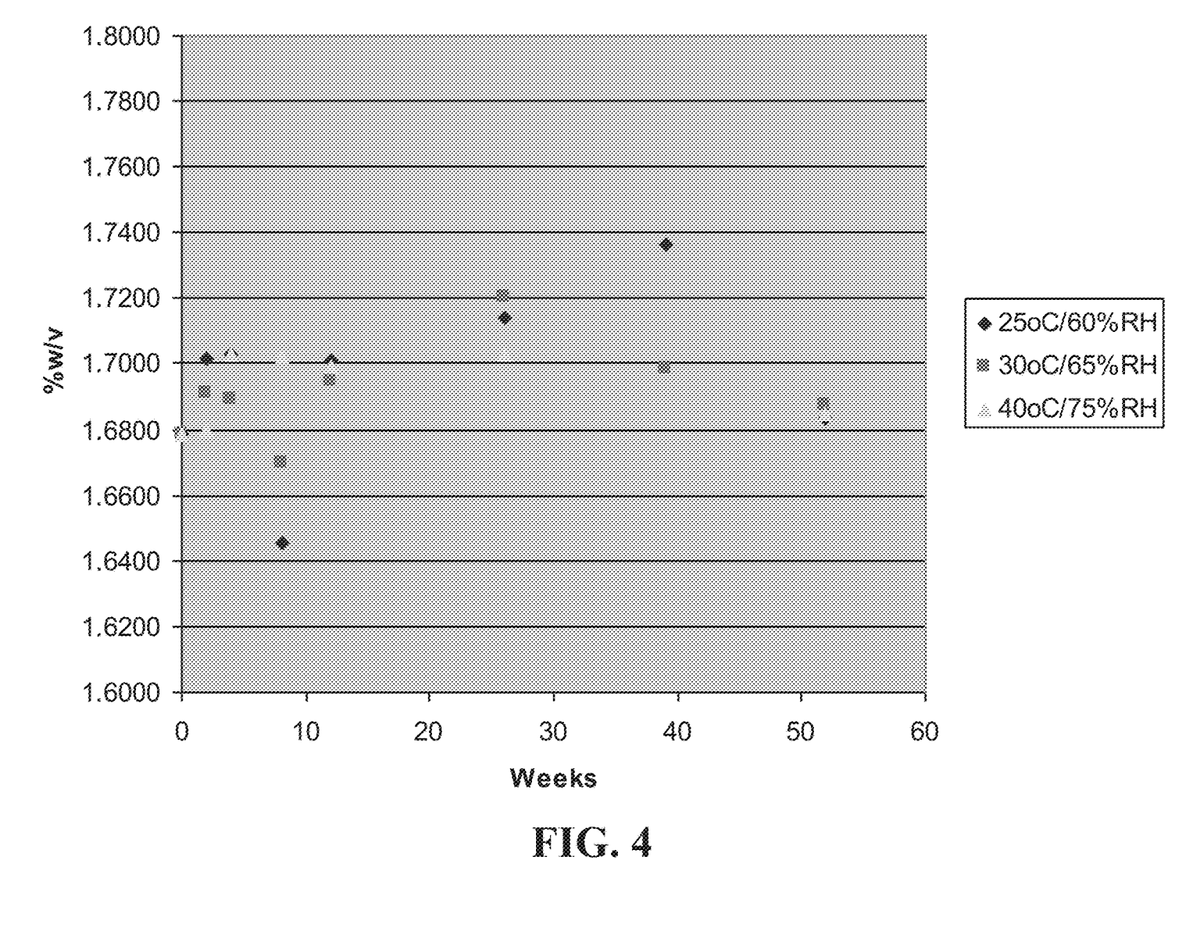
FIG. 4 illustrates degradation studies on Example 4 of the present invention.
Figure 5:
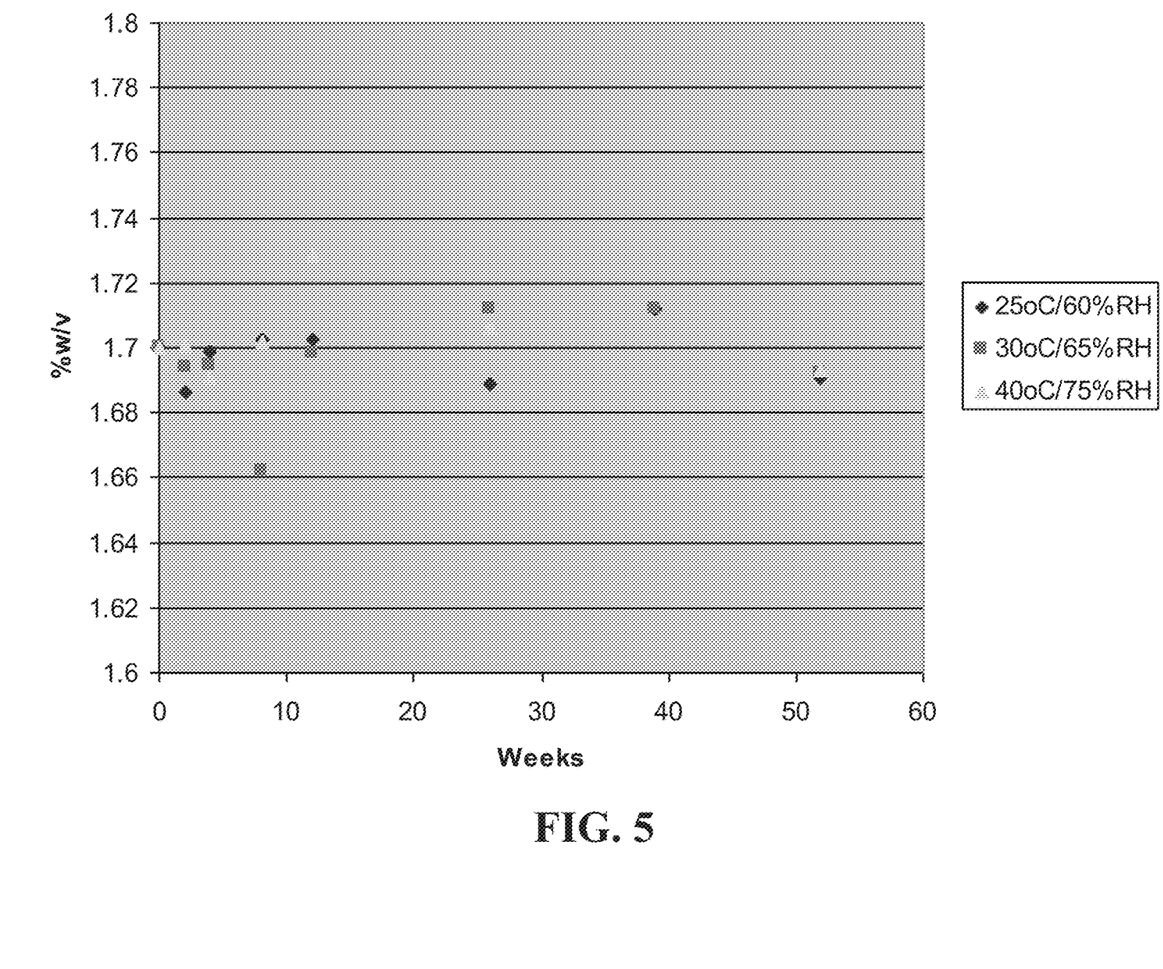
FIG. 5 illustrates degradation studies on Example 5 of the present invention.

FIGS. 4 and 5 illustrated the improved stability for the compositions of Examples 2 and 4 of the present invention. There is no significant degradation of flurbiprofen up to 52 weeks even at 40° C./75% RH. The results are given in the table below. Test compositions which contained ethanol showed degradation of between 10% and 14% within two weeks.

| Storage Conditions | Time points | Example 4 Flurbiprofen Content (% mg per ml) | Example 2 Flurbiprofen Content (% mg per ml) |
| --- | --- | --- | --- |
| 25° C./60% RH | 0 | 1.6788 | 1.6997 |
| | 2 | 1.7014 | 1.6863 |
| | 4 | 1.7029 | 1.6989 |
| | 8 | 1.6456 | 1.7027 |
| | 12 | 1.7011 | 1.7024 |
| | 26 | 1.7142 | 1.6886 |
| | 39 | 1.7365 | 1.7115 |
| | 52 | 1.6832 | 1.6908 |

-continued

| Time points | Example 4 Flurbiprofen Content (% mg per ml) | Example 2 Flurbiprofen Content (% mg per ml) |
|---|---|---|
| 30° C./65% RH | | |
| 2 | 1.6912 | 1.6939 |
| 4 | 1.6889 | 1.6941 |
| 8 | 1.6698 | 1.6622 |
| 12 | 1.6945 | 1.6979 |
| 26 | 1.7204 | 1.7117 |
| 39 | 1.6982 | 1.7115 |
| 52 | 1.6870 | 1.6922 |
| 40° C./75% RH | | |
| 2 | 1.6798 | 1.7004 |
| 4 | 1.7028 | 1.6904 |
| 8 | 1.7022 | 1.7019 |
| 12 | 1.6992 | 1.7286 |
| 26 | 1.7030 | 1.7060 |
| 52 | 1.6845 | 1.6930 |

An advantage of the present invention is that there is provided a clear physically and chemically stable solution of flurbiprofen of sufficient concentration to be used in a throat spray product, where the clinically optimized dose of active pharmaceutical substance can be delivered/metered by a pump or other spray mechanism in a small volume of (concentrated) solution together with a method of preparation. Such a solution does not exhibit the undesirable taste associated with compositions that are at higher pH, i.e. above about pH 8.

A further advantage of the present invention is that there is avoided the use of an alcohol as a co-solvent thus resulting in a composition with improved stability. The presence of an alcohol in a composition containing an NSAID with a carboxylic acid moiety results in the production of the corresponding ester. The compositions of the present invention do exhibit unexpected stability in the presence of other hydroxyl-containing compounds that are not solvents. For example, the flavor system used in the example embodiments does not result in higher levels of degradation of the flurbiprofen.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A liquid throat spray composition for topical application to a sore throat consisting essentially of an aqueous solution of at least 1% w/v of flurbiprofen, a cyclodextrin, and a pharmaceutically acceptable buffer,
   wherein the molar ratio of the NSAID to the cyclodextrin is between 1:0.5 and 1:1.5; and
   wherein the composition is provided in a unit volume of up to about 2 ml.

2. The liquid throat spray composition as claimed in claim 1, wherein the cyclodextrin is selected from the group consisting of α, β, and γ cyclodextrin.

3. The liquid throat spray composition as claimed in claim 1, wherein the cyclodextrin is selected from the group consisting of hydroxyethyl, hydroxypropyl and dihydroxypropyl ethers.

4. The liquid throat spray composition as claimed in claim 1, wherein the cyclodextrin comprises a cyclodextrin derivative selected from the group consisting of methyl α cyclodextrin, hydroxyethyl α cyclodextrin, hydroxypropyl α cyclodextrin, dihydroxypropyl α cyclodextrin, methyl β cyclodextrin, hydroxyethyl β cyclodextrin, hydroxypropyl β cyclodextrin, dihydroxypropyl β cyclodextrin, methyl γ cyclodextrin, hydroxyethyl γ cyclodextrin, hydroxypropyl γ cyclodextrin and dihydroxypropyl γ cyclodextrin.

5. The liquid throat spray composition as claimed in claim 1, wherein the composition comprises the flurbiprofen at a level of between 1-5% w/v.

6. The liquid throat spray composition as claimed in claim 1, wherein the composition contains no more than 3.2% w/v flurbiprofen.

7. The liquid throat spray composition as claimed in claim 1, wherein the amount of flurbiprofen is 1.6% w/v.

8. The A liquid throat spray composition as claimed in claim 1, wherein the amount of flurbiprofen is 3.13% w/v.

9. The liquid throat spray composition as claimed in claim 1, wherein the molar ratio of the flurbiprofen to the cyclodextrin is between 1:0.7 and 1:1.1.

10. The liquid throat spray composition as claimed in claim 1, wherein the pH of the composition is from about 6 to about 9.

11. The liquid throat spray composition as claimed in claim 1 further comprising a thickening agent.

12. The liquid throat spray composition as claimed in claim 1 further comprising one or more of pH adjusters, emulsifiers, dispersing agents, preservatives, sweeteners, and flavorants.

13. The liquid throat spray composition as claimed in claim 1, wherein the composition consists essentially of:
   1-5% w/w flurbiprofen;
   5-10% w/w of one or more α, β, and γ cyclodextrins;
   up to 5% w/v of one or more pharmaceutically acceptable aqueous buffers; and
   80-90% w/w water.

14. The liquid throat spray composition as claimed in claim 1, wherein the cyclodextrin is selected from the group consisting of natural cyclodextrins.

15. The liquid throat spray composition as claimed in claim 1, wherein the cyclodextrin is selected from the group consisting of hydroxyethyl, 2- and 3-hydroxypropyl, their corresponding mixed ethers, and mixed ethers with methyl or ethyl groups selected from the group consisting of methyl-hydroxyethyl, ethyl-hydroxyethyl and ethyl-hydroxypropyl ethers of α, β, γ-cyclodextrin.

16. The liquid throat spray composition as claimed in claim 1 further comprising a thickening agent selected from the group consisting of hydroxy ethyl cellulose, hydroxy propyl methyl cellulose, sodium carboxy methyl cellulose, and hydroxy propyl cellulose.

17. The liquid throat spray composition as claimed in claim 1, wherein the pharmaceutically acceptable buffer is present at a concentration in the range from about 0.03% to about 5.0% w/v.

18. The liquid throat spray composition as claimed in claim 1, wherein the pharmaceutically acceptable buffer is present at a concentration of about 0.1% to about 2.0% w/v.

19. The liquid throat spray composition as claimed in claim 1, wherein the pharmaceutically acceptable buffer is selected from the group consisting of phosphates, ascorbates, acetates, citrates, tartrates, lactates, succinates, amino acids and maleates.

20. The liquid throat spray composition as claimed in claim 1, wherein the pharmaceutically acceptable buffer is selected from the group consisting of disodium hydrogen orthophosphate, citric acid, and combinations thereof.

21. The liquid throat spray composition as claimed in claim 13, wherein the pH of the liquid throat spray composition is from about 7.2 to 7.6.

22. The liquid throat spray composition as claimed in claim 13, wherein the pH of the liquid throat spray composition is about 7.4.

23. The liquid throat spray composition as claimed in claim 13 further comprising 0-1% w/w of one or more flavorants, 0-0.2% w/w sweetener, and 0-0.5% w/w preservatives.

24. The liquid throat spray composition as claimed in claim 13 further comprising 0-0.5% w/w thickening agent.

25. The liquid throat spray composition as claimed in claim 1, wherein the cyclodextrin is selected from the group consisting of alkylated derivatives, hydroxyalkylated derivatives, and branched cyclodextrin derivatives bearing sugar residues.

26. The liquid throat spray composition as claimed in claim 13, wherein the pharmaceutically acceptable aqueous buffer is present at a concentration in the range from about 0.03% to about 5.0% w/v.

27. The liquid throat spray composition as claimed in claim 1, wherein the pH of the liquid throat spray composition is from about 7.2 to 7.6.

28. The liquid throat spray composition as claimed in claim 1, wherein the pH of the liquid throat spray composition is about 7.4.

* * * * *

UNITED STATES PATENT AND TRADEMARK OFFICE
CERTIFICATE OF CORRECTION

PATENT NO. : 10,363,316 B2  
APPLICATION NO. : 14/859619  
DATED : July 30, 2019  
INVENTOR(S) : Edward Beech, Alden Rodwell and Mark Squires Page 1 of 1

It is certified that error appears in the above-identified patent and that said Letters Patent is hereby corrected as shown below:

On the Title Page

Item (73), Assignee, please replace "Reckitt Benckiser Healthcare (UK) Limited" with -- Reckitt Benckiser Healthcare International Limited --

Signed and Sealed this  
Second Day of June, 2020

Andrei Iancu  
*Director of the United States Patent and Trademark Office*